(12) United States Patent
Imataka et al.

(10) Patent No.: US 8,445,232 B2
(45) Date of Patent: *May 21, 2013

(54) CELL-FREE SYSTEM FOR SYNTHESIS OF PROTEINS DERIVED FROM CULTURED MAMMALIAN CELLS

(75) Inventors: Hiroaki Imataka, Yokohama (JP); Satoshi Mikami, Yokohama (JP); Shigeyuki Yokoyama, Yokohama (JP)

(73) Assignee: Riken, Saitama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/211,280

(22) Filed: Aug. 16, 2011

(65) Prior Publication Data

US 2011/0300575 A1 Dec. 8, 2011

Related U.S. Application Data

(63) Continuation of application No. 11/798,759, filed on May 16, 2007, now Pat. No. 8,012,712, which is a continuation of application No. PCT/JP2005/020959, filed on Nov. 15, 2005.

(30) Foreign Application Priority Data

Nov. 17, 2004 (JP) ................................ 2004-333250

(51) Int. Cl.
*C12P 21/00* (2006.01)
(52) U.S. Cl.
USPC ...................................... 435/69.1; 514/21.92
(58) Field of Classification Search
None
See application file for complete search history.

(56) References Cited

U.S. PATENT DOCUMENTS

| 5,264,341 | A | 11/1993 | Maciak et al. |
| 5,270,181 | A | 12/1993 | McCoy et al. |
| 5,532,151 | A | 7/1996 | Chantry et al. |
| 5,674,729 | A | 10/1997 | Wimmer et al. |
| 5,800,984 | A | 9/1998 | Vary |
| 5,804,374 | A | 9/1998 | Baltimore et al. |
| 5,869,286 | A | 2/1999 | Yao et al. |
| 5,959,085 | A | 9/1999 | Garrone et al. |
| 5,962,246 | A | 10/1999 | Ladner et al. |
| 6,136,568 | A | 10/2000 | Hiatt et al. |
| 6,303,337 | B1 | 10/2001 | Rothschild et al. |
| 6,511,832 | B1 | 1/2003 | Guarino et al. |
| 6,780,607 | B2 | 8/2004 | Choi et al. |
| 6,800,453 | B2 * | 10/2004 | Labaer et al. ................ 435/68.1 |
| 7,195,895 | B2 | 3/2007 | Motoda et al. |
| 7,348,134 | B2 | 3/2008 | Lingappa et al. |
| 2002/0025525 | A1 | 2/2002 | Shuber |
| 2002/0142387 | A1 | 10/2002 | Seki et al. |
| 2003/0050453 | A1 | 3/2003 | Sorge |
| 2003/0068651 | A1 * | 4/2003 | Arrowsmith et al. .......... 435/7.1 |
| 2004/0121346 | A1 | 6/2004 | Endo et al. |
| 2004/0137448 | A1 | 7/2004 | Thornton et al. |
| 2005/0095705 | A1 | 5/2005 | Kadan et al. |
| 2005/0244920 | A1 | 11/2005 | Shirouzu et al. |
| 2007/0281337 | A1 | 12/2007 | Imataka et al. |

FOREIGN PATENT DOCUMENTS

| EP | 0469610 A1 | 2/1992 |
| EP | 1143009 A1 | 10/2001 |
| EP | 1176210 A1 | 1/2002 |
| EP | 1316616 A1 | 6/2003 |
| EP | 1354959 A1 | 10/2003 |
| EP | 1857558 A1 | 11/2007 |
| JP | 4-200390 A | 7/1992 |
| JP | 7-110236 A | 4/1995 |
| JP | 9-107954 A | 4/1997 |
| JP | 09-234074 A | 9/1997 |
| JP | 2000-175695 A | 6/2000 |
| JP | 2000-325076 A | 11/2000 |
| JP | 2002-238595 A | 8/2002 |
| JP | 2003-18999 A | 1/2003 |
| JP | 2003-235598 A | 8/2003 |
| JP | 2004-91790 A | 3/2004 |
| JP | 2004-215651 A | 8/2004 |
| JP | 2004-267205 A | 9/2004 |
| JP | 2004-290181 A | 10/2004 |
| JP | 2005-6646 A | 1/2005 |
| JP | 2005-225796 A | 8/2005 |
| WO | WO-88/08453 A1 | 11/1988 |
| WO | WO-92/07949 A1 | 5/1992 |
| WO | WO-92/11390 A1 | 7/1992 |
| WO | WO-92/13955 A1 | 8/1992 |
| WO | WO-97/46696 A1 | 12/1997 |

(Continued)

OTHER PUBLICATIONS

Sasaki, Y., et al., 1995, "Effect of non-dialyzable extract of amaranth seeds on immunoglobulin production and proliferation of human-human hybridoma cell line, HF10B4", Nippon Shokuhin Kagaku Kogaku Kaishi, vol. 42, No. 11, pp. 937-944.*

(Continued)

*Primary Examiner* — Manjunath Rao
*Assistant Examiner* — William W Moore
(74) *Attorney, Agent, or Firm* — Birch, Stewart, Kolasch & Birch, LLP (57) ABSTRACT

Prepared is an extract composition having an improved protein synthetic activity in a cell-free protein synthesis system using a mammalian cultured cell extract. An eukaryotic translation initiation factor and/or translational regulator are added to a cell-free protein synthesis system comprising an extract prepared from cultured mammalian cells and a template mRNA. These factors are one or more selected from the group consisting of eukaryotic translation initiation factors 4E (eIF4E), 2 (eIF2) and 2B (eIF2B), and eukaryotic translational regulator p97.

11 Claims, 7 Drawing Sheets

FOREIGN PATENT DOCUMENTS

| | | |
|---|---|---|
| WO | WO-99/02671 A1 | 1/1999 |
| WO | WO-99/14370 A1 | 3/1999 |
| WO | WO-99/20798 A1 | 4/1999 |
| WO | WO-99/57992 A1 | 11/1999 |
| WO | WO-00/56914 A1 | 9/2000 |
| WO | WO-01/83805 A2 | 11/2001 |
| WO | WO-02/18586 A1 | 3/2002 |
| WO | WO-02/090537 A1 | 11/2002 |
| WO | WO-03/097829 A1 | 11/2003 |

OTHER PUBLICATIONS

Ishihara et al., "Expression of G protein coupled receptors in a cell-free translational system using detergents and thioredoxin-fusion vectors", Protein Expression and Purification, vol. 41, pp. 27-37, 2005.

Kalmbach et al., "Functional Cell-free Synthesis of a Seven Helix Membrane Protein: In situ Insertion of a Bacteriorhodopsin Into Liposomes", J. Mol. Biol., vol. 371, pp. 639-648, 2007.

Wieder K. J. et al., "Cell-free translation of a biologically active antigen-specific supressor T cell factor," Proc. Natl. Acad. of Sci. USA, vol. 79, pp. 3599-3603 (1982).

Giller et al., "A homologous in vitro system to analyze transcription of a mouse immunoglobulin μ heavy-chain gene", Eur. J. Biochem., vol. 172, pp. 679-685, 1988.

Nishimura et al., "Enhancement of Protein Synthesis in Continuous-Flow, Cell-Free System by Improvement of Membrane Permeation", Journal of Fermentation and Bioengineering, vol. 80, No. 4, pp. 403-405, 1995.

Sigma-Aldrich product catalog page for Polyoxyethylene 23 lauryl ether (Brij 35).

Bochkareva et al., "Chaperonin-promoted Post-translational Membrane Insertion of a Multispanning Membrane Protein Lactose Permease", Journal of Biological Chemistry, vol. 271, No. 36, pp. 22256-22261, 1996.

Wheatley et al., "Glycosylation of G-protein-coupled receptors for hormones central to normal reproductive functioning: its occurrence and role", Human Reproduction Update, vol. 5, No. 4, pp. 356-364, 1999.

Kigawa et al., "Cell-free production and stable-isotope labeling of milligram quantities of proteins", FEBS Letters, vol. 442, pp. 15-19, 1999.

Booth et al., Biochemical Society Transactions, vol. 28, Part 3, p. A50, 2000.

Kigawa et al., "High-throughput Cell-free Protein Expression System for Structural Proteomics", Protein, Nucleic Acid and Enzyme, vol. 47, No. 8, pp. 1014-1020, 2002.

Kain et al., "Universal Promoter for Gene Expression Without Cloning: Expression-PCR", BioTechniques, vol. 10, No. 3, pp. 366-368 and 370, 1991, XP000912135.

MacFerrin et al., "Overproduction and dissection of proteins by the expression-cassette polymerase chain reaction", Proc. Natl. Acad. Sci., vol. 87, No. 5, pp. 1937-1941, 1990, XP000268593.

Ohuchi et al., "In vitro method for the generation of protein libraries using PCR amplification of a single DNA molecule and coupled transcription/translation", Nucleic Acids Research, vol. 26, No. 19, pp. 4339-4346, (1998) XP002119037.

Nakano et al., "Efficient Coupled Transcription/Translation from PCR Template by a Hollow-Fiber Membrane Bioreactor", Biotechnology and Bioengineering, vol. 64, No. 2, pp. 194-199, (1998) XP001084028.

Sandhu et al., "Dual Asymmetric PCR: One-Step Construction of Synthetic Genes", BioTechniques, vol. 12, No. 1, pp. 14-16, 1992, XP002134139.

Horton et al., "Engineering hybrid genes without the use of restriction enzymes: gene splicing by overlap extension", Gene, vol. 77, pp. 61-68, 1989, XP002090392.

Liu et al., "Functional characterization of novel human ARFGAP3", FEBS Letters, vol. 490, Nos. 1-2, pp. 79-83, 2001.

Laage et al., "Strategies for Prokaryotic Expression of Eukaryotic Membrane Proteins", Traffic, vol. 2, No. 2, pp. 99-104, 2001.

Yoshida et al., "In Vitro Synthesis of Hyaluronan by a Single Protein Derived from Mouse HAS1 Gene and Characterization of Amino Acid Residues Essential for the Activity", Journal of Biological Chemistry, vol. 275, No. 1, pp. 497-506, 2000.

Lehto et al., "Release of the glycosylphosphatidylinositol-anchored enzyme ecto-5'-nucleotidase by phospolipase C: catalytic activation and modulation by the lipid bilayer", Biochem. Journal, vol. 332, pp. 101-109, 1998.

The pET Expression System, http://www.bio.davidson.edu/Course/Molbio?nolStudents/spring2003/Causey/p- ET.html, pp. 1-4, 2003.

Tucker et al., "Purification of a rat neurotensin receptor expressed in *Escherichia coli*", Biochem. Journal, vol. 317, pp. 891-899, 1996.

Grisshammer et al., "Expression of a rat neurotensisn receptor in *Escherichia coli*", Biochem. Journal, vol. 295, pp. 571-576, 1993.

Abdulaev et al., "Functionally Discrete Mimics of Light-activated Rhodopsin Identified through Expression of Soluble Cytoplasmic Domains", Journal of Biological Chemistry, vol. 275, No. 50, pp. 39354-39363, 2000.

Sachdev et al., "Solubility of Proteins Isolated from Inclusion Bodies is Enhanced by Fusion to Maltose-Binding Protein or Thioredoxin", Protein Expression and Purification, vol. 12, No. 1, pp. 122-132, 1998.

McIntyre et al., "Procathepsins L and D are Membrane-Bound in Acidic Microsomal Vesicles", Journal of Biological Chemistry, vol. 266, No. 23, pp. 15438-15445, 1991.

Invitrogen, "Flexible in vitro expression with high-yield results", Expressions, vol. 9, Issue 2, p. 7, 2002.

Novagen, "pET-23a-d(+) Vectors", p. 1, 1998.

Falk, "Cell-free synthesis and assembly of connexins into functional gap junction membrane channels", EMBO Journal, vol. 16, No. 10, pp. 2703-2716, 1997.

Rhee et al., "Channel-Forming Activity of Immunoaffinity-Purified Connexin32 in Single Phospholipid Membranes", Biochemistry, vol. 35, No. 28, pp. 9212-9223, 1996.

Ohtaki et al., "Expression, Purification, and Reconstitution of Receptor for Pituitary Adenylate Cyclase-activating Polypeptide", Journal of Biological Chemistry, vol. 273, No. 5, 15464-15473, 1998.

Mambetisaeva et al., "Expression of Three Functional Domains of Connexin 32 as Thioredoxin Fusion Proteins in *Escherichia coli* and Generation of Antibodies", Protein Expression and Purification, vol. 11, No. 1, pp. 26-34, 1997.

Peng et al., "Cystic fibrosis transmembrane conductance regulator: expression and helicity of a double membrane-spanning segment", FEBS Letters, vol. 413, No. 1, pp. 29-33, 1998.

Potapov et al., "Correlation between poly(U) misreading and poly(dT) translation efficiency in *E coli* cell-free systems", Biochimie, vol. 72, pp. 345-349, 1990.

Okamoto-Hosoya et al., "An aberrant protein synthesis activity is linked with antibiotic overproduction in *rpsL* mutants of *Streptomyces coelicolor* A3(2)", Microbiology, vol. 149, pp. 3299-3309, 2003.

Hu et al., "Novel Approach for Improving the Productivity of Antibiotic-Producing Strains by Inducing Combined Resistant Mutations", Applied and Environmental Microbiology, pp. 1885-1892, 2001.

Hosoya et al., "Acquisition of Certain Streptomycin-Resistant (str) Mutations Enhances Antibiotic Production in Bacteria", Antimicrobial Agents and Chemotherapy, vol. 42, pp. 2041-2047, 1998.

Chumpolkulwong et al., "Effects of *Escherichia coli* ribosomal protein S12 mutations on cell-free protein synthesis", Eur. J. Biochem., vol. 271, pp. 1127-1134, 2004.

Hwang, Y.-I., "Mutant 30S ribosomal subunit S12", Database EMBL, Oct. 1, 2002, XP-00235355.

Office Action mailed Jan. 13, 2009 in Japanese Application No. 2002-345597.

Inaoka et al., "Construction of an In Vivo Nonsense Readthrough Assay System and Functional Analysis of Ribosomal Proteins S12, S4, and S5 in *Bacillus subtillis*", Journal of Bacteriology, vol. 183, No. 17, pp. 4958-4963, 2001.

Funatsu et al., "Ribosomal Proteins: Location of Amino-acid Replacements in Protein S12 isolated from *Escherichia coli* Mutants Resistant to Streptomycin", J. Mol. Biol., vol. 68, pp. 547-550, 1972.

Timms et al., "Mutant sequences in the *rpsL* gene of *Escherichia coli* B/r: mechanistic implications for spontaneous and ultraviolet light mutagenesis", Molecular and General Genetics, vol. 232, pp. 89-96, 1992.

Shehata et al., "Effect of Temperature on the Size of *Escherichia coli* Cells", Journal of Bacteriology, vol. 124, No. 2, pp. 857-862, 1975.

Patterson et al., "Deductive Analysis of a Protein-Synthesis Mutant of *Escherichia coli*", Biochemical Genetics, vol. 8, No. 2, pp. 205-230, 1973.

Klammt et al., "Cell-Free Production of Integral Membrane Proteins on a Preparative Scale", Methods in Molecular Biology, vol. 375, pp. 57-78, 2007.

Mathews et al., "Mammalian Cell-Free Protein Synthesis Directed by Viral Riboonucleic Acid", Eur. J. Biochem. vol. 17, pp. 328-338, 1970.

Zawada et al., "Effects of Genotype and Growth Conditions on Cell-Free Protein Synthesis Systems", Abstracts of Papers of the American Chemical Society, vol. 224, Nos. 1-2, p. BIOT 91, 2002, XP009068071.

Jones et al., "Function of a Relaxed-Like State following Temperature Downshifts in *Escherichia coli*", Journal of Bacteriology, vol. 174, No. 12, pp. 3903-3914, 1992.

Zubay, G., "In vitro synthesis of protein in microbial systems", Annual Review of Genetics, vol. 7, pp. 267-287, 1973.

Wang et al., "An Optimized Yeast Cell-Free System: Sufficient for Translation of Human Papillomavirus 58 L1 mRNA and Assembly of Virus-like Particles", Journal of Bioscience and Bioengineering, vol. 106, No. 1, pp. 8-15, 2008.

Hofbauer et al., "Preparation of a mRNA-Dependent Cell-Free Translation System from Whole Cells of *Saccharomyces cerevisiae*", Eur. J. Biochem. vol. 122, pp. 199-203, 1982.

Kim et al., "Expression-independent consumption of substrates in cell-free expression system from *Echerichia coli*", Journal of Biotechnology, vol. 84, pp. 27-32, 2000.

Kim et al., "Continuous Cell-Free Protein Synthesis Using Glycolytic Intermediates as Energy Sources", J. Microbiol. Biotechnol., vol. 18, No. 5, 885-888, 2008.

Ertola et al., "Design, Formulation, and Optimization of Media", Bioprocess Technol., vol. 21, pp. 89-137, 1995.

Lee et al., "Statistical Medium Formulation and Process Modeling by Mixture Design of Experiment for Peptide Overexpression in Recombinant *Escherichia coli*", Applied Biochemistry and Biotechnology, vol. 135, pp. 81-100, 2006.

Lee et al., "Enhanced specific antibody productivity of calcium alginate-entrapped hybridoma is cell line-specific", Cytotechnology, vol. 16, pp. 1-15, 1994.

Sitaraman et al., "A novel cell-free protein synthesis system", Journal of Biotechnology, vol. 110, pp. 257-263, 2004.

Kim et al., "A highly efficient cell-free protein synthesis system from *Escherichia coli*", Eur. J. Biochem., vol. 239, pp. 881-886, 1996.

Kigawa et al., "Preparation of *Escherichia coli* cell extract for highly productive cell-free protein expression", Journal of Structural and Functional Genomics, vol. 5, pp. 63-68, 2004.

Ha et al., "Immunostimulation with *Escherichia coli* extract: prevention of recurrent urinary tract infections", International Journal of Antimicrobial Agents, vol. 31S, pp. S63-S67, 2008.

Giuliodori et al., "Preferential translation of cold-shock mRNAs during cold adaptation", RNA, vol. 10, pp. 265-276, 2004.

Nishimura et al., "Cell-Free System Derived from Heat-Schocked *Escherichia coli*: Synthesis of Enzyme Protein Possessing Higher Activity", Journal of Fermentation and Bioengineering, vol. 79, No. 2, pp. 131-135, 1995.

Yu et al., "An efficient recombination system for chromosome engineering in *Escherichia coli*", PNAS, vol. 97, No. 11, pp. 5978-5983, 2000.

Rowen et al., NCBI Protein AAF 02829, Submitted Apr. 25, 1999, Multimegabase Sequencing Center, University of Washington.

Pratt et al., "Identification of gene products programmed by restriction endonuclease DNA fragments using an *E. coli* in vitro system", Nucleic Acids Research, vol. 9, No. 18, pp. 4459-4474, 1981.

Benzinger et al., "Transfection of *Escherichia coli* Spheroplasts", Journal of Virology, vol. 15, No. 4, pp. 861-871, 1975.

Lorenz et al., "Bacterial Gene Transfer by Natural Genetic Transformation in the Environment", Microbiological Reviews, vol. 58, No. 3, pp. 563-602, 1994.

Yang et al., "Cell-free coupled transcription-translation system for investigation of linear DNA segments", Proc. Natl. Acad. Sci., vol. 77, No. 12, pp. 7029-7033, 1980.

Office Action mailed Sep. 14, 2010 in Japanese Application No. 2004-335514.

Hendrickson, W., "Determination of Macromolecular Structures from Anomalous Diffraction of Synchrotron Radiation", Science, vol. 254, No. 5028, pp. 51-58, 1991.

Spirin et al., "A Continuous Cell-Free Translation System Capable of Producing Polypeptides in High Yield", Science, vol. 242, No. 4882, pp. 1162-1164, 1988.

Ge et al., "Simultaneous Introduction of Multiple Mutations Using Overlap Extension PCR", BioTechniques, vol. 22, No. 1, pp. 28 and 30, 1997.

Kigawa et al., "Cell-free synthesis and amino acid-selective stable isotope labeling of proteins for NMR analysis", Journal of Biomolecular NMR, vol. 6, No. 2, pp. 129-134, 1995.

Ikura M., "Heteronuclear 3D NMR and isotopic labeling of calmodulin. Towards the complete assignment of the $^1$H NRM spectrum", Biochem. Pharmacol., vol. 40, No. 1, pp. 153-160, 1990.

Patzlaff et al., "An isotope-edited FT-IpaIR study of a symporter, the lactose permease", Biochem., vol. 41, pp. 7366-7372, 2002.

Ikura et al., "A Novel Approach for Sequential Assignment of $^1$H, $^{13}$C, and $^{15}$N Spectra of Larger Proteins: Heteronuclear Triple-Resonance Three-Dimensional NMR Spectroscopy. Application to Calmodulin", Biochemistry, vol. 29, pp. 4659-4667, 1990.

Bulleid et al., "Cell-free synthesis of enzymically active tissue-type plasminogen activator", Biochem. J., vol. 286, pp. 275-280, 1992.

Emmerich et al., "Characterisation of Protein Synthesis in Cell-Free Extracts from Different Mammalian Cells by their Sensitivity to Inhibitors of Polypeptide-Chain Initiation", Hoppe-Seyler's Z. Physiol. Chem., vol. 360, No. 8, pp. 1099-1111, 1979.

Svitkin et al., "Complete Transition of the Hepatitis C Virus Genome In Vitro: Membranes Play a Critical Role in the Maturation of all Virus Proteins Except for NS3", J. Virol., vol. 79, No. 11, pp. 6868-6881, (2005).

Evdokimova et al., "The major mRNA-associated protein YB-1 is a potent 5' cap-dependent mRNA stabilizer", The EMBO Journal, vol. 20, No. 19, pp. 5491-5502, 2001.

Kodukula et al., "Biosynthesis of Phosphatidylinositol-Glycan (PI-G)-Anchored Membrane Proteins in Cell-Free Systems: PI-G is an Obligatory Cosubstrate for COOH-Terminal Processing of Nascent Proteins", Proc. Natl. Acad. Sci., vol. 89, No. 11, pp. 4982-4985, 1992.

Merola et al., "Folding of Hepatitis C Virus E1 Glycoprotein in a Cell-Free System", Journal of Virology, vol. 75, No. 22, pp. 11205-11217, 2001.

Abstract of Mikami et al., "Protein Expression and Purification", 2005.

Bergamini et al., "Picornavirus IRESes and the poly(A) tail jointly promote cap-independent translation in a mammalian cell-free system", RNA, vol. 6, pp. 1781-1790, 2000.

Carroll et al., "Preparation of a Cell-Free Translation System with Minimal Loss of Initiation Factor eIF-2/eIF-2B Activity", Analytical Biochemistry, vol. 212, pp. 17-23, 1993.

Cooper et al., "Transcription of Vaccinia Virus mRNA Coupled to Translation In Vitro", Virology, vol. 88, No. 1, pp. 149-165, 1978.

Cosgrove et al., "Absence of age differences in protein synthesis by rat brain, measured with an initiating cell-free system", Neurobiology of Aging, vol. 8, No. 1, pp. 27-34, 1987.

Dougherty et al., "Translation of Potyvirus RNA in a Rabbit Reticulocyte Lysate: Reaction Conditions and Identification of Capsid Protein as One of the Products of in Vitro Translation of Tobacco Etch and Pepper Mottle Viral RNAs", Virology, vol. 101, No. 2, pp. 466-474, 1980.

Henis-Korenblit et al., "The caspase-cleaved DAP5 protein supports internal ribosome entry site-mediated translation of death proteins", PNAS, vol. 99, No. 8, pp. 5400-5405, 2002.

Imataka et al., "A new translational regulator with homology to eukaryotic translation initiation factor 4G", EMBO Journal, vol. 16, No. 4, pp. 817-825, 1997.

Imataka et al., "A newly identified N-terminal amino acid sequence of human eIF4G binds poly(A)-binding protein and functions in poly(A)-dependent translation", EMBO Journal, vol. 17, No. 24, pp. 7480-7489, 1998.

Mikami et al., "An efficient mammalian cell-free translation system supplemented with translation factors", Protein Expression and Purification, vol. 46, pp. 348-357, 2006.

Office Action mailed Aug. 10, 2010 in Japanese Application No. 2004-333250.

Mori et al., "Cell-free Translation of Carbamyl Phosphate Synthetase I and Ornithine Transcarbamylase Messenger RNAs of Rat Liver", Journal of Biological Chemistry, vol. 256, No. 8, pp. 4127-4132, 1981.

Morley et al., "A rabbit reticulocyte factor which stimulates protein synthesis in several mammalian cell-free systems", Biochimica et Biophysica Acta, vol. 825, pp. 57-69, 1985.

Nevins et al., "Distinct Regulation of Internal Ribosome Entry Site-mediated Translation following Cellular Stress is Medicated by Apoptotic Fragments of eIF4G Translation Initiation Factor Family Members eIF4GI and p97/DAP5/NAT1", Journal of Biological Chemistry, vol. 278, No. 6, pp. 3572-3579, 2003.

Pain et al., "Analysis of Translational Activity of Extracts Derived from Oocytes and Eggs of *Xenopus laevis*", Methods in Molecular Biology, vol. 77, pp. 194-209, 1998, XP008075553.

Pelham et al., "An Efficient mRNA-Dependent Translation System from Reticulocyte Lysates", Eur. J. Biochem., vol. 67, pp. 247-256, 1976.

Person et al., "Translation in Micrococcal Nuclease-Treated Cell-Free Extracts from Ehrlich Ascites Tumor Cells", Biochimica et Biophysica Acta, vol. 783, pp. 152-157, 1984.

Pestova et al., "The Structure and function of initiation factors in eukaryotic protein synthesis", Cell. Mol. Life Sci., vol. 57, pp. 651-674, 2000.

Preiss et al., "Starting the protein synthesis machine: eukaryotic translation initiation", BioEssays, vol. 25, No. 12, pp. 1201-1211, 2003.

Thoma et al., "A Poly(A) Tail-Responsive In Vitro System for Cap- or IRES-Driven Translation from HeLa Cells", Methods in Molecular Biol., vol. 257, pp. 171-180, 2004, XP002496677.

Walter et al., "Preparation of Microsomal Membranes for Cotranslational Protein Translocation", Methods in Enzymology, vol. 96, pp. 87-93, 1983.

Weber et al., "Inhibition of Protein Synthesis by Cl-", Journal of Biological Chemistry, vol. 252, No. 11, pp. 4007-4010, 1977.

Scheper et al., "Eukaryotic Initiation Factors-4E and -4F Stimulate 5' cap-dependent as well as Internal Initiation of Protein Synthesis", Journal of Biological Chemistry, vol. 267, No. 11, pp. 7269-7274, 1992.

Scheper et al., "The 5' untranslated region of encephalomyocarditis virus contains a sequence for very efficient binding of eukaryotic initiation factro eIF-2/2B", Biochimica et Biophysica Acta, vol. 1089, pp. 220-226, 1991.

Svitkin et al., "Poly(A)-binding protein interaction with eIF4G stimulates picornavirus IRES-dependent translation", RNA, vol. 7, pp. 1743-1752, 2001.

Hardwick et al., "Cell-free protein synthesis by kidney from the aging female fischer F344 rat", Biochimica et Biophysica Acta, vol. 652, No. 1, pp. 204-217, 1981.

\* cited by examiner

CELL-FREE SYSTEM FOR SYNTHESIS OF PROTEINS DERIVED FROM CULTURED MAMMALIAN CELLS

CROSS-REFERENCE TO RELATED APPLICATIONS

This application is a continuation application of U.S. application Ser. No. 11/798,759, filed May 16, 2007 and issued Sep. 6, 2011 as U.S. Pat. No. 8,012,712. U.S. application Ser. No. 11/798,759 is a continuation of International Application No. PCT/JP2005/020959, filed on Nov. 15, 2005, and claims priority to Japanese Patent Application No, 2004-333250, filed on Nov. 17, 2004, both of which are incorporated herein by reference in their entireties.

TECHNICAL FIELD

The present invention relates to a process for producing a protein in a cell-free system. More particularly, it relates to a cell-free protein synthesis system using an extract derived from cultured mammalian cells.

BACKGROUND ART

The cell-free protein synthesis system derived from cultured mammalian cells is important for analysis of gene products in eukaryotes and research of translational regulation. Most generally, rabbit reticulocyte lysate is used, and a number of proteins expressed in the system exhibit normal activities in vivo, through a correct folding and processing of those proteins (for example, see Non-Patent Document 1). Post-translational modification such as acetylation, isoprenylation or phosphorylation is required in some cases for the function or activity of proteins. Alternative post-translational modification (processing) such as cleavage of a signal peptide or addition of a carbohydrate chain has been achieved by adding a canine microsomal membrane to the above-mentioned translation reaction mixture (for example, see Non-Patent Document 2).

On the other hand, it is known that in a synthetic reaction of proteins in eukaryotes, particularly translation reaction, a far larger number of translation initiation factors are involved than in prokaryotes and their interaction is complicated. In initiation of the protein synthetic system in eukaryotes, at least ten members of eukaryotic initiation factors (eIFs) are required. In the first step in which a pre-initiation complex is formed, the GTP type of eIF2 transports an initiation tRNA (Met-tRNAi) to a small subunit of 40S ribosome. Then, the pre-initiation complex attaches to the 5'-end of eukaryotic mRNA. In this step, eIF4F (also termed as cap-binding complex consisting of eIF4E, eIF4A and eIF4G) and eIF3 are required. This complex searches for AUG nearest at the 5'-end. After binding of Met-tRNAi with the initiation AUG, the initiation factor eIF5 releases eIF2 and eIF3. Finally, a 60S subunit binds to the complex comprising the initiation tRNA, mRNA and 40S subunit to form a 80S initiation complex. It is considered that in eukaryotic cells the translation reaction is mainly regulated by such initiation factors (for example, see Non-Patent Documents 3-5).

In eukaryotic cells, it is known that mRNA as a template for protein synthesis has a cap structure ($^{m7}$GpppN) in which 7-methylguanosine binds to the 5'-end phosphate via pyrophosphate. This structure plays an important role not only in a protective action against enzymatic degradation of mRNA but also in a mechanism of initiation of translation. The translation is promoted by binding of a cap binding factor (eIF4E) to the cap structure. At the 3'-end of mRNA, there is a poly-A structure linked by 80-100 polyadenylic acids to stabilize mRNA, which structure interacts with a translation-initiating complex through a poly A binding factor (PABP). It is known that this cap structure promotes translation in a cell-free system for protein synthesis, too. In order to provide a cap structure at the 5'-end of mRNA in vitro, a cap-like material designated as cap analogue is used as a substrate for synthesizing a cap-carrying mRNA by enzymatic reaction with RNA polymerase. When this capped mRNA is used to synthesize a protein, however, since the coexisting cap analogue has an inhibitory action to the protein synthesis, an additional manipulation for removing the cap analogue from mRNA preparation is required. In addition, there is a problem in using a cap analogue that the amount of synthesized mRNA is reduced.

Non-Patent Document 1: Pelham, H R. and Jackson, R J., "An efficient mRNA-dependent translation system from reticulocyte lysates", (1976) Eur J Biochem. Vol. 67, pp. 247-256.

Non-Patent Document 2: Walter, P. and Blobel, G. (1983) Method, Enzymol., Vol. 96, pp. 84

Non-Patent Document 3: Imataka, H. et al., (1997) EMBO J. Vol. 16, pp. 817-825

Non-Patent Document 4: Imataka, H. et al., (1998) EMBO J. Vol. 17, pp. 7480-7489

Non-Patent Document 5: Svitkin, Y V, et al., (2001) RNA Vol. 7, pp. 1743-1752

SUMMARY OF THE DISCLOSURE

Rabbit reticulocyte lysate is available as a number of commercial products, but they are expensive and activities thereof have lot-to-lot variances because of using animals. In order to maintain a stable synthetic activity of protein without sacrifice of animals, a system derived from culture cells such as HeLa cell has been developed, but in general it has been believed that the rabbit reticulocyte lysate has much higher protein synthetic activity. Thus, the invention is directed to produce an extract composition that has an improved protein synthesis activity in a cell-free protein synthesis system using a mammalian cultured cell extract.

The present invention was accomplished to solve the above-mentioned problems. The present inventors succeeded in obtaining a protein synthetic activity comparable to or higher than that of rabbit reticulocyte lysate by adding a certain translation initiation factor or translational regulator to an extract from cultured mammalian cells. The inventors further investigated on various members of translation initiation factors or translation regulators to be added and found that higher translation activity can also be obtained even by using mRNA having no cap structure. The present invention was completed based on these findings.

In a first aspect of the present invention, a process for producing a protein in cell-free protein synthesis system is provided, which comprises adding a template mRNA and an eukaryotic translation initiation factor to an extract prepared from cultured mammalian cells. The above-mentioned translation initiation factor is preferably one or more selected from the group consisting of a translation initiation factor 4E(eIF4E), translation initiation factor 2(eIF2), and translation initiation factor 2B(eIF2B).

In an example, the above-mentioned template mRNA has a cap structure at 5'-end thereof.

In another example, the process for producing a protein in the invention comprises adding one or both of translation initiation factor 2 (eIF2) and translation initiation factor 2B (eIF2B) into a cell-free protein synthetic system containing an extract prepared from cultured mammalian cells and a template mRNA having an internal ribosome entry site (IRES) of picornavirus at the 5'-end.

In yet another example, the process for producing a protein in the invention comprises adding an un-capped template mRNA and one or more factors selected from the group consisting of eukaryotic translation initiation factors 2(eIF2) and 2B(eIF2B) and an eukaryotic translation regulator p97, into an extract prepared from cultured mammalian cells.

In an alternative aspect of the present invention, there is provided a composition for use in synthesis of a protein using a cell-free system, comprising an extract of cultured mammalian cells and one or more eukaryotic translation initiation factors selected from the group consisting of translation initiation factor 4E (eIF4E), translation initiation factor 2(eIF2), and translation initiation factor 2B(eIF2B).

The meritorious effects of the present invention are summarized as follows.

According to the invention, it is possible to construct a cell-free protein synthesis system having a high protein synthetic activity by adding the above-mentioned particular eukaryotic translation initiation factor and/or translation regulator to an extract prepared from cultured mammalian cells. Further, a template mRNA can be produced at low costs since a high translation activity can be obtained without capping at the 5'-end of mRNA.

PREFERRED MODES OF THE INVENTION

Definitions

In a method of the present invention, the phrase "cell-free protein synthesis system" is a system to synthesize a target protein by preparing an extract including protein factors necessary for translation of proteins, and reconstituting the reaction in vitro. The extracts derived from a variety of organisms can be used for constituting the cell-free system, for example, those of eukaryotic and prokaryotic cells with high protein synthetic activities, such as bacteria including *E. coli*, thermophilic bacteria and the like, wheat germ, rabbit reticulocyte, mouse L cell, Ehrlich's ascitic cancer cell, HeLa cell, CHO cell and budding yeast and the like (see, Clemens, M. J., Transcription and Translation—A Practical Approach, (1984), pp. 231-270; Henes, B. D. et al. eds., IRL Press, Oxford).

The term "eukaryotic translation initiation factor (eIF)" refers to a protein factor that is necessary for initiation of protein synthesis in eukaryotes, and more than ten kinds thereof are known to exist. The initiation step of eukaryotic translation includes significantly complicated reactions in contrast to that of prokaryote, which has only three initiation factors. These eukaryotic translation initiation factors include eIF3, eIF4 and eIF6 that bind to a subunit of ribosome, eIF4B, eIF4E, eIF4A and eIF4G that are concerned with binding to mRNA, eIF2 and eIF2B that are related to transporting an initiation tRNA, eIF5 that dissociates other factors, and the like. On the other hand, it is known that there is a factor that regulates the translation by some mechanism such as an interaction with the translation initiation factors, although such a factor is not indispensable in the eukaryotic translation initiation. For example, p97 appears to suppress or enhance the translation activity by binding to eIF4A and eIF3. In the present specification, these factors are referred to as "eukaryotic translational regulator".

The term "template mRNA" means an mRNA encoding a desired protein to be expressed. The term "picornavirus" refers to a virus having a single and positive-stranded RNA ("picornavirus" literally means small RNA virus) with an icosahedral particle (capsid). The family Picornaviridae is separated into at least four distinct genera such as Genus *Enterovirus*, Genus *Rhinovirus*, Genus *Aphthovirus* that relates to animal diseases, and Genus *Cardiovirus*.

[Eukaryotic Translation Initiation Factors and Translation Regulators]

The cell-free protein synthesis system of the invention comprises an extract of cultured mammalian cells which are eukaryotic cells, and a template mRNA, to which an eukaryotic translation initiation factor and/or a translation regulator (hereinafter referred to as translation initiation factors and the like (eIF etc.)) are added. In an example, the translation initiation factors and the like to be added to the above cell-free protein synthesis system include at least one selected from the group consisting of translation initiation factors eIF2, eIF2B and eIF4E, and translation regulator p97. eIF2 is a heterotrimer GTP-binding protein which transports an initiation tRNA to the 40S ribosomal subunit. The nucleotide sequences of mRNA encoding the three human eIF2 subunits, α: 36 kDa, β: 38 kDa and γ: 52 kDa have been registered as Accession Nos. NM_004094, NM_003908 and NM_001415, respectively, on the database of GenBank.

eIF2B catalyzes the reaction to convert eIF2-GDP to eIF2-GTP, and it is composed of 5 different subunits. It has been reported that FLAG-tag is attached on the respective subunits and the resulting proteins can be expressed in Sf9 cells infected with baculovirus and purified to be reconstituted as eIF2B having a guanine nucleotide converting activity (see Fabian, J. R. et al., J. Biol. Chem. Vol. 272, No. 19, pp. 12359-12365, 1997). The nucleotide sequences of mRNAs encoding each subunit of human eIF2B have been registered as Accession Nos. NM_001414 (eIF2B1), NM_014239 (eIF2B2), NM_020365 (eIF2B3), Q9UI10 (eIF2B4), and XM_291076 (eIF2B5), respectively, on the database of GenBank.

eIF4E is a constituent of a cap-binding complex, eIF4F, and a factor directly binding to the cap structure. It is known that eIF4E is essential for cap-depending translation initiation and excessive expression thereof in NIH3T3 cells causes malignant transformation of the cells (see Lazaris-Karatzas, A et al., Nature (1990) 345:544-547). The nucleotide sequence of mRNA encoding murine eIF4E has been registered as Accession no. NM_007917 on the database of GenBank. eIF4G works as a scaffold of eIF4E and eIF4A to form eIF4F. eIF4A works as RNA-dependent ATPase and as ATP-dependent RNA helicase. It has been considered to unwind the secondary structure of the 5' untranslated region of mRNA so that ribosome can readily bind thereto.

p97 is a translation regulator homologous to the translation initiation factor eIF4G. Human p97 protein is composed of 907 amino acid residues, which has approximately 28% homology with the ⅔ C-terminal portion of eIF4G (see above-mentioned non-patent document 3). The entire coding region of mRNA has been registered as Accession no. U73824 on the database of DDBJ/EMBL/GenBank. At first, it was considered to control the translation of a capped mRNA in the living cells, but it was first found in the invention to enhance the translation of non-capped mRNA in a cell-free system.

These translation initiation factors etc., except eIF2, can easily be obtained by recombinant DNA techniques. For example, genes encoding them are cloned and linked (inserted) to a suitable vector to yield an expression vector. This expression vector is then transformed to suitable host cells, and the resulting transformants are cultured to yield the respective translation initiation factors etc. In this situation, the above-mentioned translation initiation factors etc. include those derived from human being but are not particularly limited as far as they are derived from mammals. In addition, it is natural that, though the amino acid sequences of the translation initiation factors etc. prepared by the above method contain deletion, substitution or addition of one or more amino acids, such proteins may be employed in the method of the invention as far as they have the respective activities as translation initiation factors etc. In addition, in these translation initiation factors etc., a histidine tag or FLAG tag may be added for the purpose of easy purification.

Though the host organisms are not particularly limited as far as they allow replication and maintenance of the above expression vectors; for example, bacteria such as *Escherichia coli*, *Bacillus subtilis*, etc., Yeasts such as *Saccharomyces cerevisiae*, *Schizosaccharomyces pombe*, etc., and additionally animal cells such as COS cells, CHO cells, etc., or insect cells such as Sf9, Sf21, etc., may be used.

When a bacterium such as *Escherichia coli* is used as a host, it is preferred that a recombinant vector into which genes such as translation initiation factors are introduced can be self-replicated in the bacterium and the vector is further composed of promoter, ribosome-binding sequence, a gene of translation initiation factors, and a replication-terminating sequence. In addition, a promoter-regulating gene may be contained.

*Escherichia coli* is exemplified by *Escherichia coli* K12, DH1, etc.; and *Bacillus* includes for example *Bacillus subtilis*. Any type of promoters may be used as far as they can be expressed in a host such as *Escherichia coli*. For example, promoters derived from Escherichia coli or phage, such as trp promoter, lac promoter, $P_L$ promoter, $P_R$ promoter, etc. may be used. An artificially designed and improved promoter such as tac promoter may be used. As for the method for introducing a recombinant vector into bacteria, there is no particular limitation as far as it allows introduction of DNA into bacteria. For example, a method of using calcium ion (Cohen, S. N, et al. (1972) Proc. Natl. Acad. Sci., USA 69, 2110-2114), electroporation and the like are included.

When a yeast is used as a host, *Saccharomyces cerevisiae*, *Schizosaccharomycespombe*, *Pichiapastoris*, and the like maybe used. In this case, there is no particular limitation in promoters to be used as far as they can be expressed in yeasts; for example, gal1 promoter, gal10 promoter, heat-shock protein promoter, MFα1 promoter, PHO5 promoter, PGK promoter, GAP promoter, ADH promoter, AOX1 promoter, and the like are exemplified. As for the method for introducing a recombinant vector into yeasts, there is no particular limitation as far as it allows introduction of DNA into yeasts. For example, an electroporation method (Becker, D. M. et al., (1990) Methods Enzymol., 194, 182-187), a spheroplast method (Hinnen, A. et al., (1978) Proc. Natl. Acad. Sci., USA 75, 1929-1933), a lithium acetate method (Itoh, H. (1983) J. Bacteriol. 153, 163-168), and the like are exemplified.

When an animal cell is used as a host, simian cell COS-7, Vero, Chinese hamster ovary cell (CHO cell), murine L cell, rat GH3, human FL cell, and the like may be used. As for promoters, SRα promoter, SV40 promoter, LTR promoter, CMV promoter, and the like may be used. Additionally, an early gene promoter of human cytomegalovirus may also be used. As for the method for introducing a recombinant vector into animal cells, for example, electoroporation, calcium phosphate method, lipofection method, and the like may be used.

When an insect cell is used as a host, Sf9 cell, Sf21 cell, and the like are used. Introduction of a recombinant vector into insect cells may be effected for example by a calcium phosphate method, lipofection method, electroporation, and the like.

The transformants obtained from animal cells as host may be incubated on a generally used culture medium such as RPMI1640 medium, DMEM medium, or a medium prepared by adding calf serum to these media. The culture is usually carried out at 37° C. in the presence of 5% $CO_2$ for a period of 1-30 days. During culture, an antibiotic such as kanamycin or penicillin if required may be added to the culture medium. When the coexistence of serum is inappropriate, a serum-free medium may be used depending on the purpose.

When the desired translation initiation factors etc. are produced within the cells, after incubation, the cells are disrupted to extract the translation initiation factor etc. When the desired translation initiation factors etc. are produced outside of the cells, the culture broth is used as such or the cells are removed by centrifugation and the like. Thereafter, the translation initiation factors etc. may be isolated from the above culture product and purified by means of a conventional biochemical technique usually used in isolation and purification of the translation initiation factors etc., for example, precipitation with ammonium sulfate, gel chromatography, ion exchange chromatography, affinity chromatography, and the like, alone or in their combination.

[Template mRNA]

As for the template mRNA used in the invention, there is no particular limitation as far as it codes for the protein desired to be expressed; it may be isolated directly from the cells or may be synthesized by cloning a DNA encoding the above protein to a vector containing an RNA polymerase promoter, followed by in vitro transcription reaction. A method of in vitro transcription of DNA cloned after the phage polymerase promoter is known (Krieg, P. and Melton, D., Nucl. Acids Res., Vol. 12, p. 7057, 1984). In this method, a gene of which expression is desired is cloned to a vector containing any one of promoters among SP6, T7, and T3 RNA polymerase. Subsequently, the gene cloned in this vector is linearized at the 3'-end with a restriction enzyme and transcribed to mRNA by in vitro transcription reaction. A large number of vectors containing SP6, T7, and T3 RNA polymerase promoters have been commercialized and readily available. Thus synthesized template mRNA may or may not contain a cap structure at the 5'-end. When a cap is added to the 5'-end, a cap-like material designated as cap analogue may be used as a substrate to synthesize a cap-carrying mRNA by an enzymatic reaction with RNA polymerase.

In an example of the invention, the template mRNA has an internal ribosome entry site (IRES) of picornavirus added at the 5'-end. It is known that the translation reaction of mRNA of picornavirus is initiated by using the internal ribosome entry site (IRES). The IRES structure of picornavirus can be classified roughly into two groups; the first one includes *Enterovirus* (e.g. *Poliovirus*) and *Rhinovirus*; and the other includes *Cardiovirus* (e.g., Encephalomyocarditis virus (EMCV)) and *Aphthovirus* (e.g., Foot-and-mouth disease virus).

Preferably, the internal ribosome entry site (IRES) of EMCV is added to the 5'-end of the template mRNA. EMCV genome is a positive RNA strand of about 7900 bases in length. The entire nucleotide sequence of EMCV genome has been registered as the GenBank Accession nos. NC_001497 and X87335. EMCV RNA works as a template for translation of its own protein in the cells, which is then used in synthesis of a negative RNA strand. EMCV RNA binds to a ribosome with the assistance of the internal ribosome entry site (IRES) which works as a binding site of a translation initiation factor eIF4G. This IRES exists in the 5' non-translation region of the EMCV RNA genome, and can be cloned, for example, by amplification of the 281st to 848th nucleotide sequence of EMCV genome by PCR.

[Preparation of a Composition for Use in Cell-free Protein Synthesis]

The extract of mammalian cells used in the method of the invention may be prepared by culturing mammalian cells and disrupting the recovered cells. Though there is no particular limitation in the mammalian cells to be used, the cells highly active in the protein synthesis are preferably employed, including for example murine L-cell, Ehrlich's ascites carcinoma cell, HeLa cell, CHO cell, and the like. HeLa S3 cell is a suspension cell derived from HeLa cell, which is particularly preferred since it is readily cultured and easily proliferated. The cultured cells can be disrupted, for example, mechanically by a known method using a homogenizer, etc. The extract is treated with Micrococcus nuclease and $CaCl_2$ to decompose endogenous mRNA to reduce the background translation to a minimum level. Then, EGTA is added for chelating $CaCl_2$, thereby inactivating the nuclease.

In an example of the present invention, the cultured mammalian cells can be disrupted by exposing to compressed inert gas (e.g. nitrogen gas) to give pressure, followed by reducing the pressure (depressurization). An apparatus for this operation, for example, Mini-Bomb Cell Disruption Chamber, has been marketed from KONTES. In this method, the cells are cooled by expanding gas without elevation of the temperature which is observed in the methods of a mechanical disruption and sonication and the like. Thus, it is possible to adjust the degree of cellular destruction by altering the pressure or equilibrium time. For example, when the cells are treated under moderate pressure for a short period of time, it is possible to disrupt cell membrane only without causing disruption of intracellular organelles. It has been reported that a high activity of glycoprotein synthesis can be obtained by preparing an extract of insect cells using this apparatus (see Tarui, H. et al., Appl. Microbiol. Biotechnol. Vol. 55, pp. 446-453, 2001).

The extracts comprise several components necessary for protein synthesis, for example, tRNAs, rRNAs, amino acids, as well as initiation factors, extension and termination factors. In addition, the translation reaction of mRNA can be optimized by adding an energy regeneration system comprising phosphocreatine kinase and phosphocreatine. Further, a mixture of amino acids may be added. Potassium acetate and magnesium acetate are also added to adjust their concentrations suitable for the translation reaction. According to the method of the invention, the translation activity of mRNA can be further increased by adding the above-mentioned eukaryotic translation initiation factors to these extracts. The concentration of each translation initiation factor to be added can be optimized at, for example, 0.01-10 µM, preferably 0.1-1 µM.

These reaction mixture or amino acid mixture for cell-free protein synthesis can be dispensed easy for use in aliquots in separate or previously mixed form, and distributed as a product. These products may be preserved in a frozen or dried state, and put on the market as a kit in suitable containers for storage and for shipment. The kits may be accompanied by an instruction manual, a positive control DNA, a vector DNA, and the like.

EXAMPLE

The invention will be explained in more detail by the following examples, which are not intended to limit the scope of the invention.

[Cell Culture]

The culture of HeLa S3 cells using a petri dish was carried out in a carbon dioxide incubator (5% $CO_2$ concentration; 37° C.) in Eagle MEM medium (SIGMA Co.) supplemented with 10% heat-inactivated fetal calf serum (ICN Biomedicals, Inc.), L-glutamine (2 mM), 1 unit/ml penicillin, and 0.1 mg/ml streptomycin.

Spinner culture in one-liter scale was carried out in a spinner flask equipped with a cell culture controller system (Cell Master Model 1700 Waken-yaku). The system was set up at a temperature of 37° C., pH 7.2, dissolved oxygen concentration of 7 ppm, and stirring rate of 50 rpm.

[Preparation of Cell Extracts]

When the cell density reached $1.0-1.5 \times 10^6$ cells/ml, the HeLa S3 cells in the culture broth were collected by centrifugation at 360×g and 4° C. for 10 minutes. The culture medium was eliminated with an aspirator, and the cells recovered from 1 L of the culture broth was moderately suspended into 80 ml of buffer (35 mM HEPES-KOH (pH 7.5 at 25° C.), 140 mM NaCl, 11 mM glucose), then transferred into two 50 ml tubes, and centrifuged at 360×g and 4° C. for 5 minutes. This operation was repeated 3 times, and then 1.5 parts (for 1 part by volume of cells) of an extraction buffer (20 mM HEPES-KOH (pH 7.5 at 25° C.), 135 mM potassium acetate, 30 mM KCl, and 1.65 mM magnesium acetate) was added to give a suspension containing about $2.5 \times 10^8$ cells/ml, which was then sealed in a Mini-Bomb Cell Disruption Chamber (KONTES). The cells were disrupted under nitrogen gas pressure of 1.0 Mpa standing in ice. After the lapse of 30 minutes, the outlet port was slowly opened and the cell homogenate was recovered at a flow rate of about 3-10 drops/sec. The resulting cell homogenate was centrifuged twice at 10,000×g and 4° C. for 5 minutes; the resulting solution (2-2.5 ml) from which the precipitate was removed was applied on a PD-10 column (Amersham) which had been equilibrated with 25 ml of extraction buffer in advance. The sample was applied by free-fall onto the column, then the extraction buffer was added, and when the solution falling down from the column changed from clear to creamy-white, about 1.7-2.0 ml was collected to use as a cell extract. The resulting solution was equally divided into small portions and flash-lyophilized with liquid nitrogen to preserve at −80° C.

[Preparation of Plasmid and mRNA]

Figure 1:
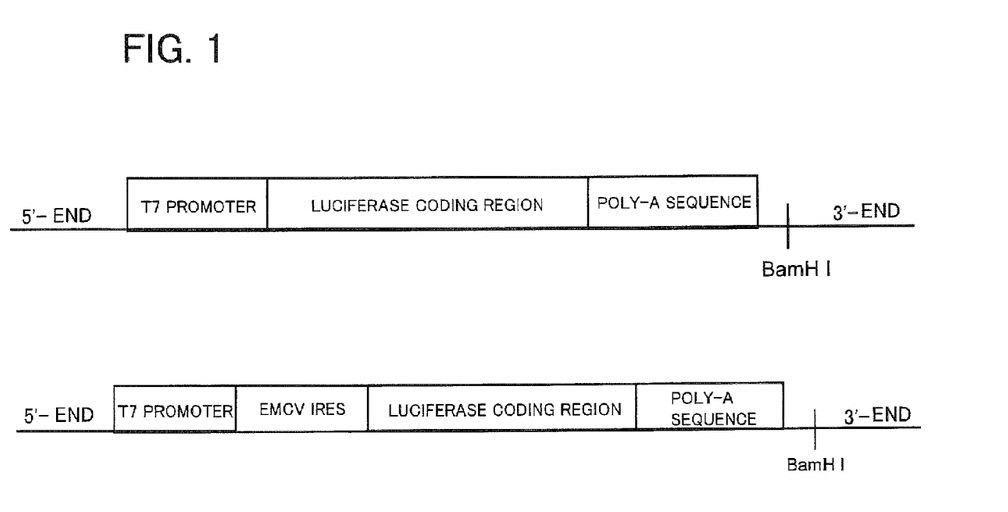
FIG. 1 schematically shows the structure of plasmid used in preparation of a variety of luciferase mRNAs used in Examples.

In order to synthesize an mRNA coding for luciferase, cap-Luc-poly-A and Luc-poly-A, cDNA of luciferase was first inserted into the downstream of T7 RNA polymerase promoter of plasmid pSP72 (Promega Co.) to yield a plasmid pSP72-Luc; and then a poly A stretch (85 deoxyadenines) was inserted into the downstream of luciferase gene to yield a plasmid pSP72-Luc-A (see the above-cited non-patent document no. 4). In order to synthesize an mRNA coding for IRES of EMCV, EMCV-Luc-poly-A, a plasmid pSP72-EMCV-Luc-A (see the above-cited non-patent document no. 5) was used. This plasmid was prepared by cloning a DNA fragment (comprising the 281st to 848th nucleotides of EMCV genome amplified by PCR using pGemCAT-EMCV-LUC (see Pause et al., Nature 371, 762-767) as a template) between a plasmid pSP72-LUC-A T7 promoter and a luciferase gene. FIG. 1 shows schematically the structure of each plasmid.

mRNAs of Luc-poly-A and EMCV-Luc-poly-A were synthesized by using as templates products derived from the above respective plasmids (cleaved at the 3'-end side of the poly-A sequences by a restriction enzyme BamHI) with T7RNA polymerase according to the method using RiboMAX Large Scale RNA Production Systems (Promega). In the synthesis of cap-Luc-poly-A mRNA, the concentration of GTP used in the above synthetic method was changed from 5.0 mM to 0.8 mM, and the reaction was conducted in a condition in which a cap structural analogue m7G (5')ppp (5')A (New England BioLabs) was added at 4 mM. The resulting each mRNA was quantitatively analyzed as concentration from the absorbance at wavelength of 260 nm and preserved at −80° C.

[Cell-free Protein Synthesis]

Prior to the translation reaction of each mRNA coding for luciferase, endogenous RNAs contained in the extract were decomposed and removed. The procedure is as follows. To 100 μl of the extract (protein concentration: 14-18 mg/ml) was added 1 μl of 7500 unit/ml nuclease S7 and 1 μl of 100 mM $CaCl_2$, and the mixture was treated at 20° C. for 5 minutes, and quenched with 8 μl of 30 mM EGTA. To this extract (110 μl) was then added 16.4 μl of an energy-mixing solution (184 mM HEPES-KOH (pH 7.5), 13.2 mM ATP, 1.32 mM GTP, 198 mM creatine phosphate, 3.3 mM spermidine, 13.2 mM magnesium acetate), 1.64 μl of 3.3 mM amino acid solution (20 kinds), 4.92 μl of 3.3 mg/ml t-RNA derived from bovine liver, and 1.8 μl of 6.0 mg/ml creatine phosphate kinase, yielding a mixture. Further, the mixture was filled in a dialysis chamber (MWCO 50 kDa, produced from regenerated cellulose) and dialyzed in 4.9 ml of outer solution (containing 600 μl of energy-mixing solution, 60 μl of 3.3 mM amino acid solution (20 kinds), 3.5 ml of extraction buffer, 21 μl of 100 mM magnesium acetate, and 27 μl of 400 mM EGTA) at 32° C. for 1.5-6 hours. In this procedure, the concentration of potassium acetate in the outer solution was altered depending on the purpose.

In the translation reaction, a necessary amount of the mixture in dialysis was first collected and allowed to stand in an ice-box. Then the ice-cooled mixture (4.5 μl) was moved into an Eppendorf tube, to which was added a potassium acetate solution and an mRNA solution in order (final volume: 6 μl) to initiate the reaction. In a case of elucidating the effect of a translation initiation factor (eIF), a necessary amount of eIF and mRNA solution in turn were added to the mixture and then the reaction was initiated. The final concentration of each component contained in the reaction mixture was as follows: 9-12 mg/ml of protein derived from the extract, 27 mM HEPES-KOH (pH 7.5), 30 μM amino acids (20 kinds), 1.2 mM ATP, 120 μM GTP, 18 mM creatine phosphate, 0.3 mM spermidine, 1.2 mM magnesium acetate, 16 mM KCl, 1.65 mM EGTA, 90 μg/ml of t-RNA derived from bovine liver, and 60 μg/ml creatine phosphate kinase. The concentrations of potassium acetate and each mRNA were altered in the range of 44-224 mM and 0-0.72 μg/6 μl, respectively, according to the condition. After incubation at 32° C. for 1 hour, the reaction mixture was immediately ice-cooled, and a part of the solution was used in determination of the luciferase activity. In determination of the activity a Luciferase Assay System (Promega Co.) was used.

Figure 2:
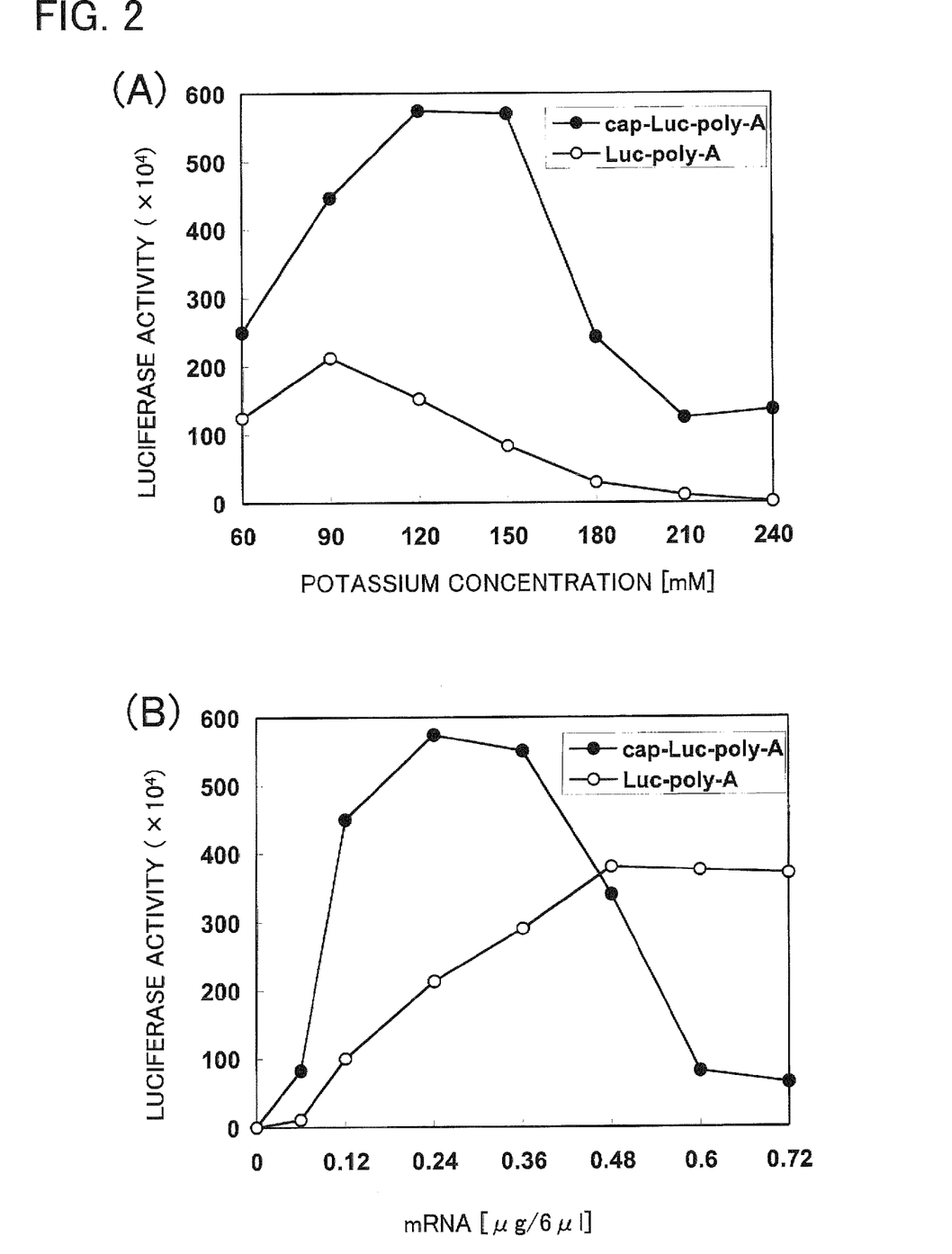
FIG. 2 shows characteristic features (potassium concentration and mRNA concentration dependency) of the translation reaction in the cell-free system using cap-Luc-poly-A and Luc-poly-A.

FIGS. 2-7 show the results. FIG. 2 shows the characteristics of the cell-free translation reaction using cap-Luc-poly-A and Luc-poly-A. In (A), HeLa S3 cell extract was treated with nuclease, and dialyzed in an outer solution of which the potassium concentration was adjusted at 80 mM, and then the translation of each mRNA (0.24 μg/6 μl concentration) was conducted in the condition of the potassium concentration as indicated in the graph. After incubation at 32° C. for 1 hour, a part of the reaction mixture was used in determination of the luciferase activity. In (B), the translation reactions for cap-Luc-poly-A and Luc-poly-A were conducted in a condition of optimal potassium concentrations, 120 mM and 90 mM, respectively, at the mRNA concentrations (0-0.72 μg/6 μl) as indicated in the graph, and the luciferase activity was determined in the same way as indicated above. The symbol ● indicates cap-Luc-poly A; and ○ indicates Luc-poly A. As shown in FIGS. 2 (A) and (B), cap-Luc-poly A having a cap structure at the 5'-end showed the highest luceferase activity at 120 mM potassium concentration and at 0.24 μg/6 μl mRNA concentration. On the other hand, Luc-poly-A which has no cap structure showed the highest activity at 90 mM potassium concentration and at 0.48 μg/6 μl mRNA concentration.

Figure 3:
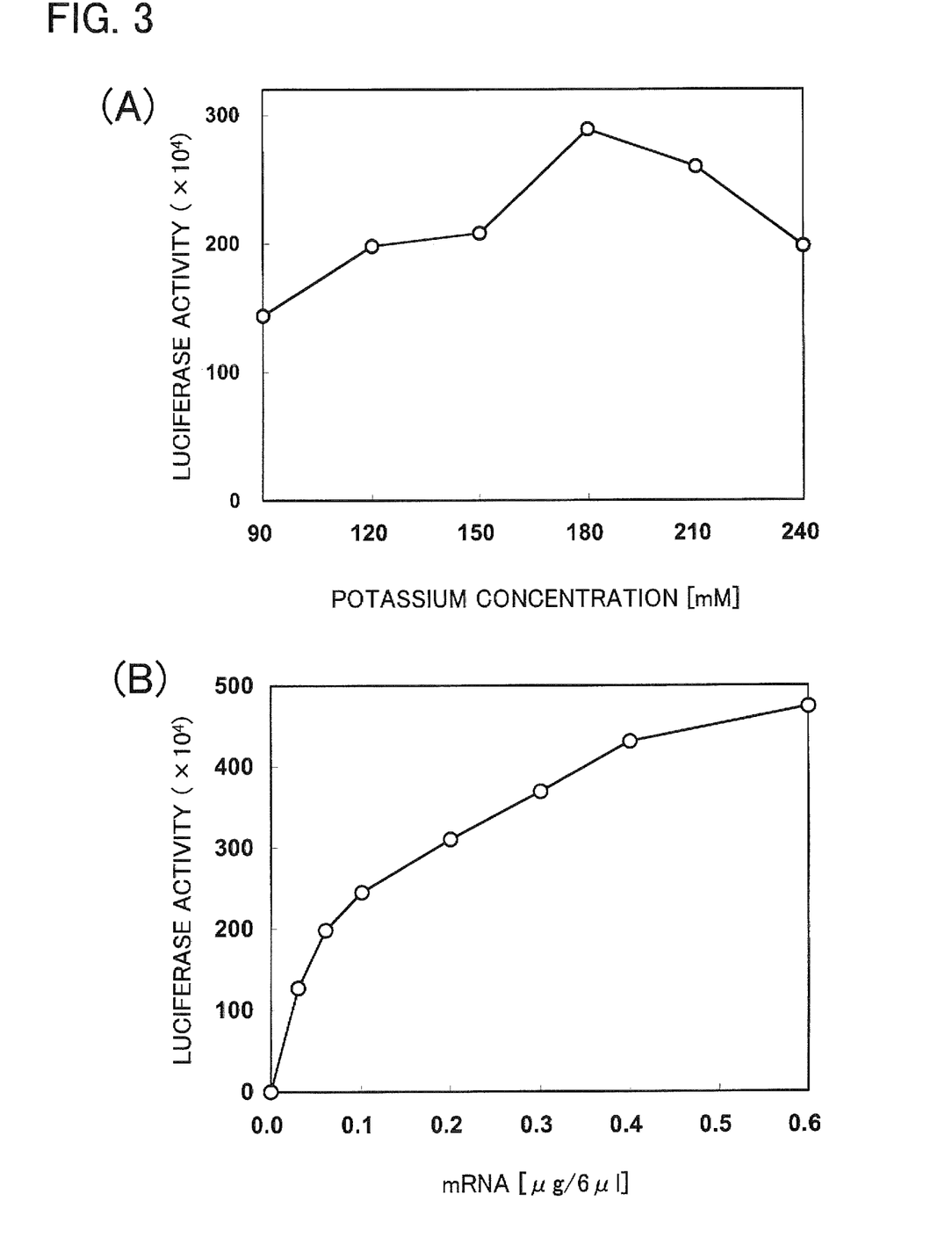
FIG. 3 shows characteristic features (potassium concentration and mRNA concentration dependency) of the translation reaction in the cell-free system using EMCV-Luc-poly-A.

Next, FIG. 3 shows the characteristics of the cell-free translation reaction using EMCV-Luc-poly-A. In (A), HeLa S3 cell extract treated with nuclease was dialyzed in an outer solution of which the potassium concentration was adjusted at 120 mM, and then the translation of mRNA (0.2 μg/6 μl) was conducted in the condition of the potassium concentration as indicated in the graph. After incubation at 32° C. for 1 hour, a part of the reaction mixture was used in determination of the luciferase activity. In (B), the translation reaction was conducted in the condition of the optimal potassium concentration (180 mM) obtained from the result in the translation of EMCV-Luc-poly-A in (A) at the mRNA concentration (0-0.6 μg/6 μl) as indicated in the graph, and the luciferase activity was determined in the same way as indicated above. As shown in FIGS. 3(A) and (B), Luc-poly A having an IRES of EMCV showed the highest luceferase activity at 180 mM potassium concentration and the activity value increased depending on the concentration of mRNA.

Figure 4:
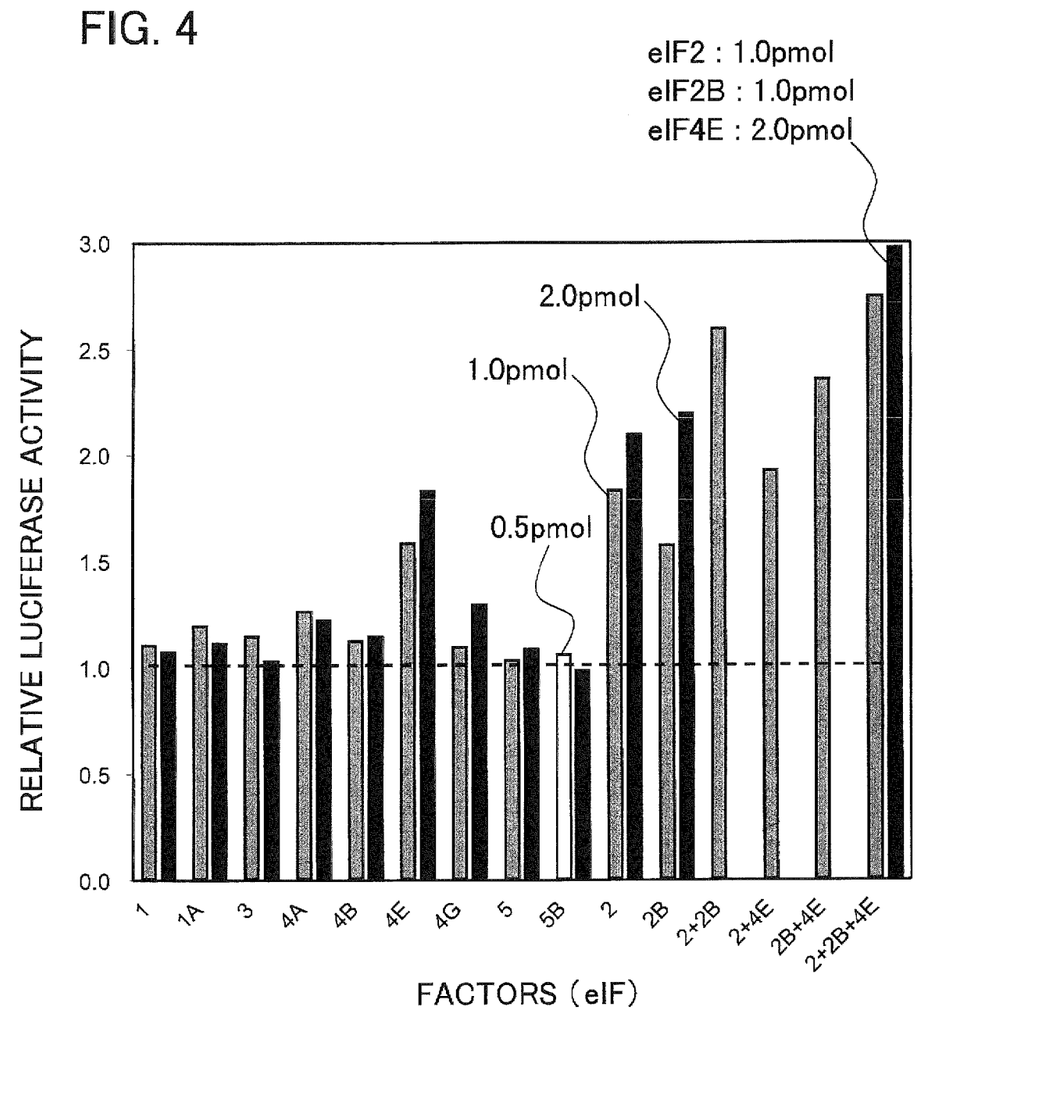
FIG. 4 shows the effect of the respective factors (eIFs) in the translation reaction in the cell-free system using cap-Luc-poly-A.

FIG. 4 shows the effects of a variety of factors (eIF) in the translation reaction of a cell-free system using cap-Luc-poly-A. The HeLa S3 cell extract treated with nuclease was dialyzed in an outer solution of which the potassium concentration was adjusted at 160 mM, to which was then added each factor as indicated in the graph, and then the translation was conducted in the optimum conditions (the concentrations of potassium and mRNA were 120 mM and 0.24 μg/6 μl, respectively). After incubation at 32° C. for 1 hour, a part of the reaction mixture was used in determination of the luciferase activity. Each reaction was repeated twice. The luciferase activity value was regarded as 1.0 when no eIF was added, and the activity value of each reaction was calculated as a ratio thereof, which was represented by the average value. The white, light gray and dark gray bars indicate that the concentrations of eIF contained in the reaction mixture are 0.5, 1.0 and 2.0 pmol, respectively. The black bar indicates that eIF2 and eIF2B each is contained at 1.0 pmol, and eIF4E at 2.0 pmol. As clearly seen from FIG. 4, the translation of mRNA having a cap at the 5'-end, i.e. cap-Luc-poly-A, showed significantly high luciferase activity when any one of eIF2, eIF2B and eIF4E or they together were added. When these 3 translation initiation factors were added together, it was found that the activity of protein synthesis was increased about 3 times in comparison with no addition.

Figure 5:
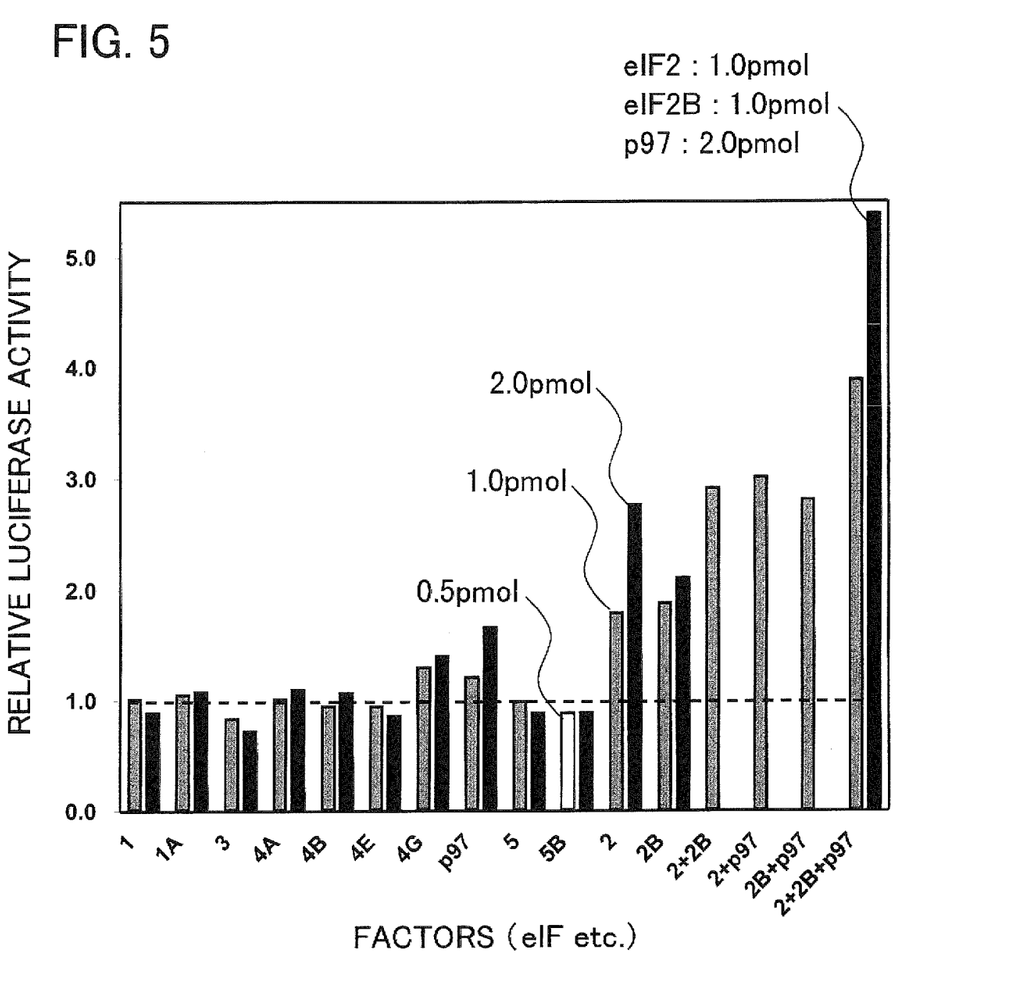
FIG. 5 shows the effect of the respective factors (eIFs etc.) in the translation reaction in the cell-free system using Luc-poly-A.

FIG. 5 shows the effects of a variety of factors (eIF etc.) in the translation reaction of a cell-free system using Luc-poly-A. The HeLa S3 cell extract treated with nuclease was dialyzed in an outer solution of which the potassium concentration was adjusted at 120 mM, to which was then added each factor as indicated in the graph, and then the translation was conducted in the optimum conditions (the concentrations of potassium and mRNA were 90 mM and 0.48 µg/6 µl, respectively). After incubation at 32° C. for 1 hour, a part of the reaction mixture was used in determination of the luciferase activity. Each reaction was repeated twice. The luciferase activity value was regarded as 1.0 when no eIF etc. was added, and the activity value of each reaction was calculated as a ratio thereof, which was represented by the average value. The white, light gray and dark gray bars indicate that the concentrations of eIF contained in the reaction mixture are 0.5, 1.0 and 2.0 pmol, respectively. The black bar indicates that eIF2 and eIF2B each is contained at 1.0 pmol, and p97 at 2.0 pmol. As seen from FIG. 5, the translation of mRNA having no cap at the 5'-end, i.e. Luc-poly-A, showed significantly high luciferase activity when any one of eIF2, eIF2B and p97 or they together were added. When these 3 translation initiation factors were added together, it was found that the activity of protein synthesis was increased 5 times or more in comparison with no addition.

Figure 6:
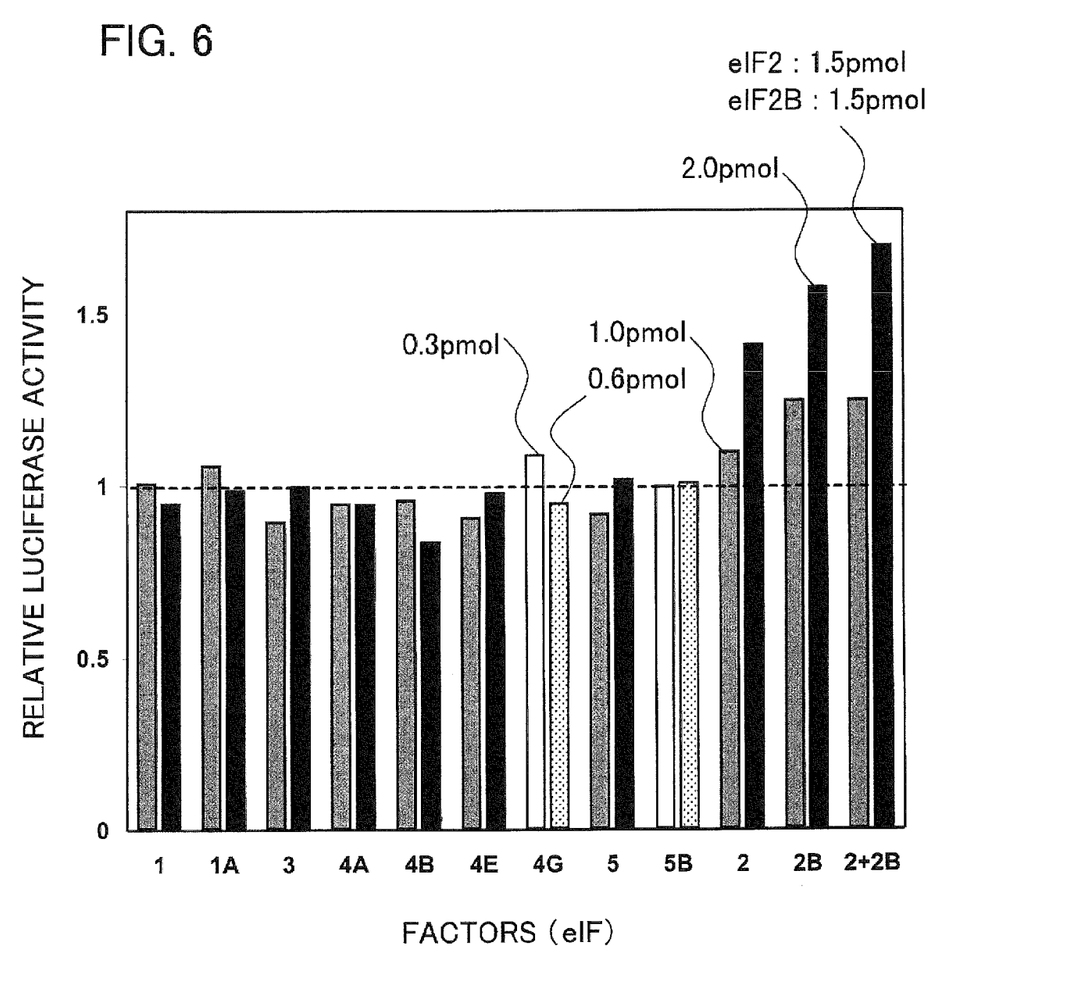
FIG. 6 shows the effect of the respective factors (eIFs) in the translation reaction in the cell-free system using EMCV-Luc-poly-A.

FIG. 6 shows the effects of a variety of factors (eIF) in the translation reaction of a cell-free system using EMCV-Luc-poly-A. The HeLa S3 cell extract treated with nuclease was dialyzed in an outer solution of which the potassium concentration was adjusted at 240 mM, to which was then added each factor as indicated in the graph, and then the translation was conducted in the optimum conditions (the concentrations of potassium and mRNA were 180 mM and 0.6 µg/6 µl, respectively). After incubation at 32° C. for 1 hour, a part of the reaction mixture was used in determination of the luciferase activity. Each reaction was repeated twice. The luciferase activity value was regarded as 1.0 when no eIF was added, and the activity value of each reaction was calculated as a ratio thereof, which was represented by the average value. The white, dotted, light gray and dark gray bars indicate that the concentrations of eIF contained in the reaction mixture are 0.3, 0.6, 1.0 and 2.0 pmol, respectively. The black bar indicates that eIF2 and eIF2B each is contained at 1.5 pmol. As seen from FIG. 6, the translation of mRNA to which was added an IRES of EMCV at the 5'-end, i.e. EMCV-Luc-poly-A, showed significantly high luciferase activity when either of eIF2 or eIF2B or both were added. When these 2 translation initiation factors were added together, it was found that the activity of protein synthesis was increased 1.5 times or more in comparison with no addition.

Figure 7:
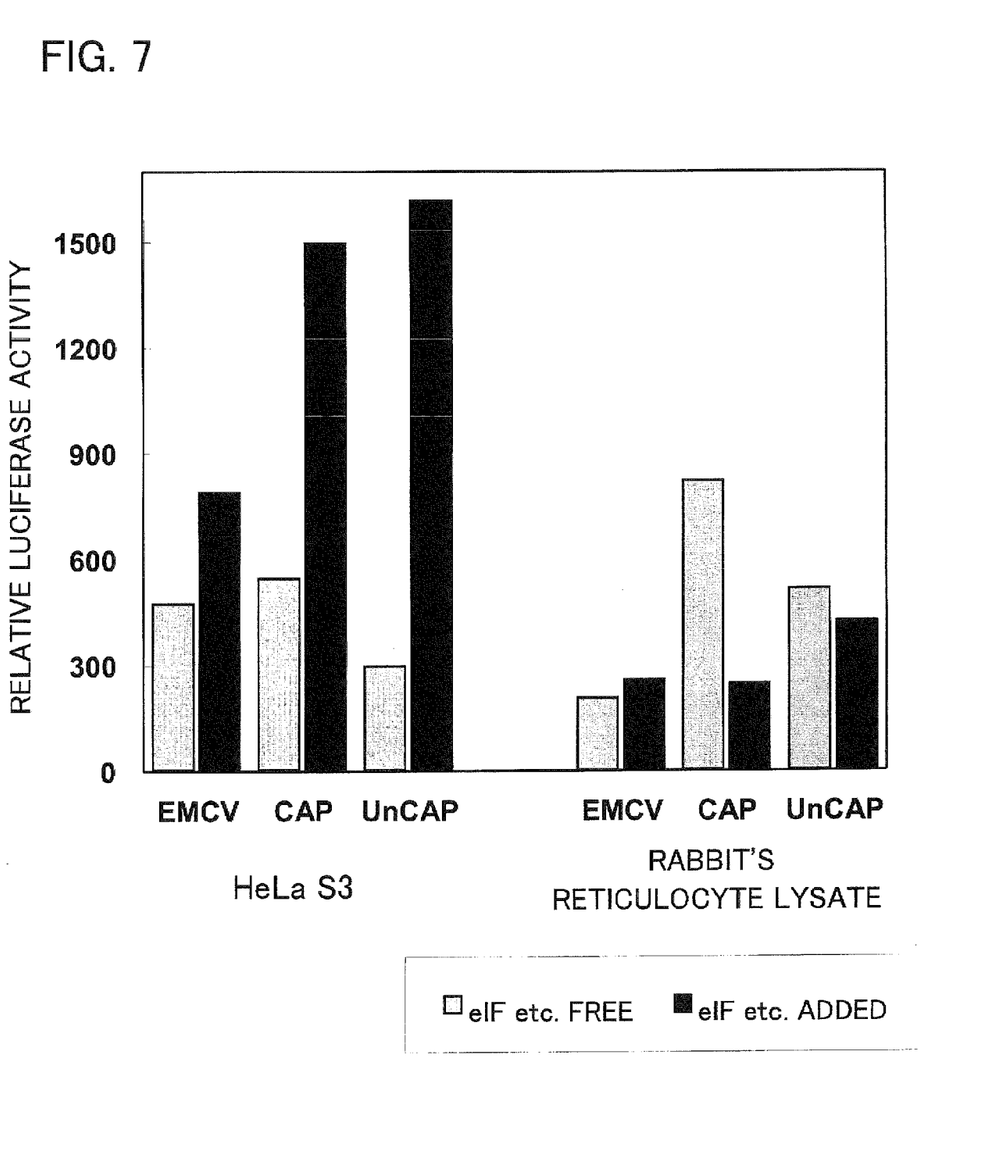
FIG. 7 shows the translation activity of the respective mRNAs in the translation reaction in the cell-free system using HeLaS3, rabbit reticulocyte lysate.

FIG. 7 shows the translation activity of each mRNA in the translation reaction of a cell-free system using HeLa S3 and rabbit reticulocyte lysate. The translation reaction was conducted in the optimum conditions for translation of each mRNA, obtained from the results of FIGS. 4-6 using HeLa S3 (no eIF etc. added; light gray), and in the condition in which the best effect was observed by addition of eIF etc.(addition of eIF etc.; black), and then the luciferase activity value was compared. That is, when EMCV-Luc-poly-A was used as a template, each 1.5 pmol of eIF2 and eIF2B was added; when cap-Luc-poly-A was used, each 1.0 pmol of eIF2 and eIF2B and 2.0 pmol of eIF4E were added; and when Luc-poly-A was used, each 1.0 pmol of eIF2 and eIF2B and 2.0 pmol of p97 were added. In addition, the results of the translation reaction of each mRNA when an extract of rabbit reticulocyte lysate (Promega) was used, was also compared at the same time. In the reaction with the extract of rabbit reticulocyte lysate, potassium acetate was supplemented at a concentration of 100, 150, and 50 mM in translation of EMCV-Luc-poly-A, cap-Luc-poly-A, and Luc-poly-A, respectively, and the incubation was carried out at 30° C. for 1 hour according to the instruction attached. All of the mRNA concentration was fixed at 0.1 µg/6 µl. As seen from FIG. 7, a higher luciferase activity was recognized in the extract of rabbit reticulocyte lysate than in HeLa S3 cells in an eIF-free condition regardless of capped or un-capped, but when a given translation initiation factor etc. was added, respectively, the protein synthesis activity was greatly increased in the HeLa S3 cell extract, and it was found that the protein was synthesized in larger quantities than in the extract of rabbit reticulocyte lysate in each condition.

REFERENCE EXAMPLE

[Preparation of eIF etc.]

The eIF etc. showing a translation-enhancing effect in the above-mentioned Example are as follows. The protein concentration in each final sample was determined by a Bradford method using BSA as a standard. No contamination of other proteins was confirmed by SDS-PAGE, followed by Coomassie blue staining.

[Preparation of eIF2]

Endogenous eIF2 isolated from HeLa cells (human) or Krebs cells (mouse) was purified to use (see Trachsel et al. (1979) Biochim. Biophys. Acta 561: 484-490).

[Preparation of eIF2B]

(1) Production of cDNA of eIF2B, Expression Plasmid, and Transformant Baculovirus:

Each cDNA was obtained by reverse transcription PCR (RT-PCR). RNA for use in RT-PCR was obtained from HeLa cells. Primer DNAs corresponding to eIF2B1 (GenBank accession number: NM_001414), eIF2B2 (no. NM_014239), eIF2B3 (no. NM_020365), eIF2B4 (no. Q9UI10), and eIF2B5 (no. XM_291076) were respectively referred to the sequences registered in GenBank. The resulting cDNAs all were sequenced and the base sequences were confirmed to be identical with those registered. In order to make purification easy, a FLAG sequence was added at the C-terminal of eIF2B3, and 6×His sequence at the N-terminal of eIF2B4. These cDNAs were inserted into a plasmid pAcDB3 (PharMingen) for use in production of baculovirus to produce pAcDB3-2B1-2B2-His2B4 and pAcDB3-2B3-FLAG-2B5. Thus produced plasmid and baculovirus DNA BaculoGold (PharMingen) were introduced into an insect cell Sf9 simultaneously. Virus in which correct recombination occurred was selected, and Baculo-2B1-2B2-his-2B4 virus and Baculo-2B3-FLAG-2B5 virus were amplified. The former virus can express eIF2B1, eIF2B2 and His-eIF2B4 simultaneously, and the latter expresses eIF2B3-FLAG and eIF2B5 simultaneously.

(2) Expression and Purification of eIF2B:

Insect cells High Five (Invitrogen Co.) were cultured in 1 L of culture medium Express FiveSFM (Invitrogen Co.) in a spinner flask equipped with a cell culture controller system (Cell master model 1700, Waken-yaku). The system was set up at a temperature of 27° C., dissolved oxygen concentration of 7.8 ppm, and stirring rate of 50 rpm. When the cell concentration reached 0.5-0.8×10⁶ cells/ml, the cells were infected with Baculo-2B1-2B2-his-2B4 and Baculo-2B3-FLAG-2B5 simultaneously. After the lapse of 50 hours, the cells were recovered, frozen at −20° C. and preserved. eIF2B was purified as follows. The frozen-preserved cells were suspended in 100 ml of buffer (0.5M KCl, 20 mM HEPES, pH 7.5, 10% glycerol, 5 mM 2-mercaptoethanol, 0.2% Triton X-100, and proteinase inhibitor "-EDTA Complete (Roche)"), allowed to stand in ice for 20 minutes, and centrifuged at 10,000×g for 20 minutes to yield a clear supernatant. Imidazole was added thereto so that the final concentration was 20 mM, and admixed with 2 ml of Ni-NTA-agarose resin (Qiagen Co.) at 4° C. After 1 hour, the mixture was passed through an empty column to remove unbound proteins. The column was further washed with the above buffer (50 ml). The bound protein was eluted with a high imidazole-containing buffer (10 ml) (0.25M imidazole, 0.15M KCl, 20 mM HEPES, pH 7.5, 10% glycerol, 5 mM 2-mercaptoethanol, 0.02% Triton X-100). EDTA was added up to 1 mM, and the mixture was concentrated to 2 ml by Amicon Ultra 30,000 MWCO (Millipore), and then added to a gel filtration column Superdex 200 HiLoad 16/60 (Amersham). Fractionation with a buffer (0.5M KCl, 20 mM HEPES, pH 7.5, 10% glycerol, 5 mM 2-mercaptoethanol, and 1 mM EDTA) gave fractions (0.3 ml/min, 1 ml/fraction) and the fractions containing each subunit were confirmed by staining with Coomassie blue and Western blotting. The fractions confirmed that all of the subunits were contained were collected and diluted 3-fold with a buffer (20 mM HEPES, pH 7.5, 10% glycerol, 5 mM 2-mercaptoethanol, and 1 mM EDTA) and added to an anti-FLAG-Agarose (Sigma Co.) column (0.2 ml). The column was washed with a buffer (5 ml) (0.1M KCl, 20 mM HEPES, pH 7.5, 10% glycerol, 5 mM 2-mercaptoethanol, 1 mM EDTA), and then eluted with the same buffer (0.7 ml) containing FLAG-peptide (Sigma Co.) (50 µg/ml) to give eIF2B. The eluted eIF2B was dialyzed in a solution (0.1M KCl, 20 mM HEPES, pH 7.5, 10% glycerol, 5 mM 2-mercaptoethanol, 0.1 mM EDTA) using a Slide-A-Lyzer Mini Dialysis unit (10,000 MWCO) (PIERCE Co.) and concentrated with a Slide-A-Lyzer Concentrating solution (PIERCE Co.).

[Preparation of eIF4E]

Murine eIF4E cDNA (Jaramillo et al. (1991) J. Biol. Chem. 266: 10446-10451) was inserted into pGEX-6P (Amersham Co.) to yield pGEX-6P-eIF4E. pGEX-6P-eIF4E was introduced into Escherichia coli BL21 (DE-3) (pLys), which was then cultured in a Luria broth (LB) until the absorbance at 600 nm reached from 0.5 to 0.9. IPTG was added (final concentration 0.1 mM), and the mixture was cultured at 30° C. for 12-16 hours to induce the expression of GST-eIF4E. The bacterium was recovered by centrifugation, washed once with a buffer (0.15M NaCl, 20 mM Tris) (50 ml), and then suspended into a buffer (0.1M KCl, 20 mM HEPES, pH 7.5, 10% glycerol, 1 mM DTT, 0.1% Triton X-100, proteinase inhibitor "Complete, Roche") (50 ml). The cells were destroyed by ultra-sonication and ultracentrifuged at 30,000 rpm (Beckman 70Ti roter) (1 hour) to remove insoluble fractions. The supernatant was admixed with Glutathione Sepharose 4B resin (Amersham Co.) (0.5 ml) and agitated at 4° C. for 1 hour. The mixture was poured into an empty column and further washed with a buffer (0.1M KCl, 20 mM HEPES, pH 7.5, 10% glycerol, 1 mM DTT, 0.1% Triton X-100, 1 mM EDTA) (30 ml) to remove unbound proteins. In this stage, GST-eIF4E is considered to still bind to the resin. PreScission Protease (12 units) (Amersham Co.) was added to the above buffer (0.5 ml), to which added the resin, and the mixture was agitated at 4° C. overnight to cleavage between GST and eIF4E in GST-eIF4E. eIF4E released from the resin was recovered and again passed through Glutathione Sepharose 4B resin (0.3 ml) to remove GST-eIF4E and GST completely. In order to further purify, the resulting eIF4E sample was bound to SP-Sepharose (0.3 ml) (Pharmacia) after adjustment of the buffer at pH 7.0. After washing with a buffer (0.1M KCl, 20 mM HEPES, pH 7.0, 10% glycerol, 5 mM 2-mercaptoethanol, 0.1 mM EDTA) (10 ml), eIF4E was eluted with the same buffer containing 0.3M KCl.

[Preparation of P97 (with FLAG Added at the C-terminal)]

A FLAG sequence was added to the C-terminal of p97 cDNA (Imataka et al. (1997) EMBO J 17: 6940-6947), and inserted into pGEX-6P to yield pGEX-6P-p97-FLAG. GST-p97-FLAG was expressed in the same manner as in GST-eIF4E. After ultracentrifugation, the supernatant was admixed with Heparin Sepharose CL-6B (0.5 ml) (Amersham Co.), and agitated at 4° C. for 1 hour. Unbound proteins were washed out in the same manner as in GST-eIF4E/Glutathione Sepharose 4B, and the bound protein was eluted with a buffer (0.5M KCl, 20 mM HEPES, pH 7.5, 10% glycerol, 1 mM DTT, 0.1% Triton X-100, 1 mM EDTA) (3 ml). The eluate was admixed with Glutathione Sepharose 4B resin (0.5 ml) and treated in the same manner as in eIF4E to yield p97-FLAG. Further, the latter was purified completely with anti-FLAG-resin in the same manner as in eIF2B.

It should be noted that other objects, features and aspects of the present invention will become apparent in the entire disclosure and that modifications may be done without departing the gist and scope of the present invention as disclosed herein and claimed as appended herewith.

Also it should be noted that any combination of the disclosed and/or claimed elements, matters and/or items may fall under the modifications aforementioned.

What is claimed is:

1. A process for producing a protein in a cell-free protein synthesis system comprising
    adding a template uncapped mRNA comprising an IRES derived from a virus nucleic acid, eukaryotic translation initiation factors 2 (eIF2) and 2B (eIF2B) and eukaryotic translational regulator p97 to an extract prepared from cultured mammalian cells and comprising 120-240 mM potassium ion, and
    incubating the mixture thereof.

2. The process of claim 1, wherein the potassium ion concentration is about 180 mM.

3. The process of claim 1, wherein said cultured mammalian cells are cultured human cells.

4. The process of claim 3, wherein said cultured human cells are cultured HeLa S3 cells.

5. A composition for synthesis of a protein using a cell-free system, comprising an extract of cultured mammalian cells and added eukaryotic translation initiation factors 2 (eIF2) and 2B (eIF2B) and added eukaryotic translational regulator p97.

6. The composition of claim 5, further comprising potassium ions at a concentration of from 120 to 240 mM.

7. The composition of claim 6, wherein said cultured mammalian cells are cultured human cells.

8. The composition of claim 7, wherein said cultured human cells are cultured HeLa S3 cells.

9. The composition of claim 5, further comprising an added eukaryotic translation initiation factor 4E and having a potassium ion concentration of from 120 to 150 mM.

10. The composition of claim 5, that provides a yield of protein from a synthesis that is about 5-fold higher than the yield obtained when the synthesis is performed in the absence of said additional eIF2, eIF2B and p97.

11. A kit for cell-free protein synthesis comprising
   i) an extract prepared from cultured mammalian cells;
   ii) isolated eukaryotic translation initiation factor 2 (eIF2);
   iii) isolated eukaryotic translation initiation factor 2E (eIF2E);
   iv) isolated eukaryotic protein synthesis regulator p97; and optionally
   v) an uncapped mRNA template comprising an IRES sequence;
   wherein each of i) and v) are packaged separately, and wherein ii), iii) and iv) may be packaged separately or as a mixture thereof.

* * * * *